United States Patent [19]

Schwarz et al.

[11] Patent Number: 4,814,435

[45] Date of Patent: Mar. 21, 1989

[54] METHOD OF PRODUCING A FACTOR VIII (AHF) CONTAINING FRACTION

[75] Inventors: Otto Schwarz; Yendra Linnau, both of Vienna, Austria

[73] Assignee: Immuno Aktiengesellschaft fur chemisch-medizinisch Produkte, Vienna, Austria

[21] Appl. No.: 108,458

[22] Filed: Oct. 15, 1987

[30] Foreign Application Priority Data

Nov. 3, 1986 [AT] Austria .................................. 2923/86

[51] Int. Cl.[4] ........................ A61K 35/16; C07K 15/14
[52] U.S. Cl. ..................................... 530/383; 424/101; 530/830; 530/387; 514/21
[58] Field of Search ..................... 530/383, 830, 387; 424/101, 85; 514/21

[56] References Cited

U.S. PATENT DOCUMENTS

| | | | |
|---|---|---|---|
| 3,973,002 | 8/1976 | Hagan et al. | 424/101 |
| 4,022,758 | 5/1977 | Andersson et al. | 530/830 X |
| 4,093,608 | 6/1978 | Iga et al. | 424/101 X |
| 4,104,266 | 8/1978 | Wickerhauser | 530/383 |
| 4,170,639 | 10/1979 | Liu et al. | 424/101 |
| 4,188,318 | 2/1980 | Shanbrom | 530/830 X |
| 4,297,344 | 10/1981 | Schwinn et al. | 424/101 |
| 4,305,871 | 12/1981 | Shanbrom | 530/830 X |
| 4,388,232 | 6/1983 | Eibl et al. | 530/383 |
| 4,440,679 | 4/1984 | Fernandes et al. | 424/85 |
| 4,486,410 | 12/1984 | Fisher | 530/382 X |
| 4,495,175 | 1/1985 | Chavin et al. | 530/830 X |
| 4,510,084 | 4/1985 | Eibl et al. | 424/101 X |
| 4,522,751 | 6/1985 | Linnau et al. | 530/383 |
| 4,543,210 | 9/1985 | Mitra et al. | 530/830 X |
| 4,687,664 | 8/1987 | Philapitsch et al. | 530/383 X |

FOREIGN PATENT DOCUMENTS

| | | |
|---|---|---|
| 8204395 | 12/1982 | PCT Int'l Appl. . |
| 1551928 | 9/1976 | United Kingdom . |
| 2120254 | 11/1983 | United Kingdom .................. 424/85 |

OTHER PUBLICATIONS

New England Journal of Medicine, vol. 273, No. 27, Dec. 30, 1965, "Production of High-Potency Concentrates of Antihemophilic...", Judith Graham Pool, and Angela E. Shannon.

*Congr. Int. Soc. Blood Transf.,* Proc. 11th, Syndey 1966, No. 29, Part 4, p. 1109, "The Preparation and Some Properties..", A. J. Johnson et al.

*Vox Sang,* v. 49, pp. 319-322, "Complexes of IgG and Plasma...", C. Wadsworth et al., 1985, Basel.

*Primary Examiner*—Howard E. Schain
*Attorney, Agent, or Firm*—Burns, Doane, Swecker & Mathis

[57] ABSTRACT

There is disclosed a method of producing a Factor VIII (AHF) containing fraction having a specific activity of at least 2.5 units of Factor VIII/mg protein as well as a portion of immunoglobulin G (IgG) of 10 mg/1000 units of Factor VIII at the most. Its risk of transmission of viral or bacterial infections is to be avoided or largely reduced. The method consists in that undesired proteins are at first precipitated from a Factor VIII (AHF) containing plasma fraction in the presence of SPS. The purified Factor VIII containing solution is treated with suitable salts or salt mixtures in order to obtain a Factor VIII containing precipitate. This precipitate is dissolved, lyophilized and finally heat-treated.

6 Claims, No Drawings

METHOD OF PRODUCING A FACTOR VIII (AHF) CONTAINING FRACTION

The invention relates to a method of producing a Factor VIII (AHF) containing fraction having a specific activity of at least 2.5 units of Factor VIII/mg protein as well as a portion of immunoglobulin G (IgG) of 10 mg/1000 units of Factor VIII at the most, at the therapeutic or prophylactic application of which the risk of transmission of viral or bacterial infections is avoided or largely reduced.

A plurality of methods for producing Factor VIII concentrates are already known from the literature. As fractionation measures, these methods involve the treatment of plasma with ethanol, ether, polyethylene glycol and/or glycine. Also known is the cryoprecipitation of plasma according to Pool (1965, "The New England Journal of Medicine" 273, 1443) or the cryoethanol precipitation of plasma according to Johnson (Congr. Int. Soc. Blood Transf., Sydney, Australia, Abstracts of Paper, p. 1109 (1966).

In U.S. Pat. No. 3,973,002, a method is, furthermore, described, with which a cryoprecipitate obtained from blood plasma is macerated, the macerated product is suspended in a citrate-glucose buffer solution, is centrifuged, and the thus obtained buffer extract is adjusted to a pH in the range of 6.0 to 6.8. Under these conditions, precipitation of undesired impurities takes place, whereupon the remaining Factor VIII containing residue is sterilized and lyophilized. However, a Factor VIII product obtained according to that method exhibits only a slight specific activity of Factor VIII units/mg of protein. In addition, the portion of immunoglobulin G (IgG), based on the Factor VIII units, is undesiredly high.

Similar methods are described in British Pat. No. 1,551,928 as well as in U.S. Pat. Nos. 4,170,639 and 4,104,266. There, likewisely by departing from plasma, a cryoprecipitate is recovered, which is dissolved in a buffer solution in the neutral pH range, with undesired proteins being separated, the supernatant being treated with aluminum hydroxide in order to separate the prothrombin complex, and the Factor VIII containing solution subsequently being concentrated and lyophilized. Even with this method, the specific activity of Factor VIII units/mg protein is undesiredly low. Thus, the specific activity when operating according to U.S. Pat. No. 4,104,266 amounts to no more than 0.5 to 0.6 units/mg protein as indicated there.

According to PCT publication WO No. 82/04395, a process for the purification and concentration of a Factor VIII complex is known, wherein the preparation is treated with a glycine solution and the supernatant is precipitated with a salt solution.

According to U.S. Pat. No. 4,522,751 of Applicant, a method for producing a Factor VIII (AHF) containing preparation with an elevated specific activity (at least 1.5 units of Factor VIII/mg protein) has been proposed, wherein the precipitation of undesired proteins is carried out in the presence of sulfated polysaccharide in the neutral range and the Factor VIII concentrate is recovered from the supernatant by alcohol precipitation.

From tests carried out recently (Vox Sang. 49: 319–322 (1985)) it has become known that IgG complexes in Factor VIII concentrates induce adverse reactions, such as lymphocyte abnormalities as well as the changes of the T helper/T suppressor cell ratio in hemophilia patients.

It has proved that the methods described yield products that, apart from the undesiredly high IgG content, are not sufficiently heat-stable in order to resist inactivation by thermal treatment without substantial loss of the Factor VIII activity. At present, there is the need to keep any coagulation factor preparations prepared from blood plasma and administered to patients in large amounts free from the risk of transmission of viral or bacterial infections, the applied inactivation methods, as a rule, involving several hour treatment at temperatures of above 60° C. This demand also holds for Factor VIII preparations, although—as known—the latter are relatively sensitive and unstable as compared to other coagulation factors.

The invention has as its object to avoid the difficulties pointed out and to provide a method of producing a Factor VIII (AHF) containing fraction in which the specific activity is raised to at least 2.5 units of Factor VIII and the portion of immunoglobulin G is as low as possible. Moreover, the preparation obtained is to be thermally stable so as to enable inactivation by heat treatment without lowering the Factor VIII activity in an undesired manner.

In accordance with the invention, this object is achieved by the combination of the following measures:

precipitating and separating undesired proteins from a solution of a plasma fraction containing Factor VIII in the presence of sulfated polysaccharides at a pH approximately in the neutral range, treating the thus purified Factor VIII containing solution with a protein precipitating agent, selected from ammonium sulfate, ammonium sulfate-glycine, sodium chloride-glycine, sodium sulfate, sodium sulfate-sodium citrate, ammonium sulfate-sodium citrate, citrate-glycine, in order to precipitate a Factor VIII containing precipitate, dissolving and lyophilizing the precipitated Factor VIII containing precipitate, and thermally treating the lyophilisate at a temperature and for a period of time sufficient to inactivate possibly present viruses.

It is known per se that the indicated salts or salt-amino acid combinations constitute protein precipitating agents and have already been used as such at the production of coagulation factor preparations, as has been illustrated by the introductory survey of the prior art.

Yet, it is the merit of the combination according to this invention to enable the recovery of products that are superior to those known so far by exhibiting a high specific activity of Factor VIII at as low an IgG content as possible and simultaneously being sufficiently heat-stable.

Preferably, the lyophilisate is adjusted to a water content of more than 0.05 (5% by weight) and less than 0.70 (70% by weight), preferably less than 0.40 (40% by weight), and is treated in a closed container at a temperature ranging from 50° to 121° C. under elevation of the steam partial pressure.

Suitably, the treatment of the lyophilisate with steam is carried out at a pressure of 0.01 to 2 bar for a period of up to 100 hours.

As the reproductive filterable pathogens, in particular, hepatitis viruses or HIV (human immune deficiency virus) are taken into consideration.

According to a preferred embodiment, the precipitation of the Factor VIII containing solution with the protein precipitating agent is effected at a pH of 5.6 to 6.8 and at a temperature of 1° to 40° C.

An advantageous embodiment of the method according to the invention is characterized by the combination of the following measures:

precipitating and separating undesired proteins from the solution of a cryoprecipitate in a citrated buffer optionally containing heparin, heparinoid, a complex compound of heparin and antithrombin III ("Atheplex") and/or aprotinin, at a pH of 6.0 to 6.4 and a temperature of 0° to 25° C., preferably 4° to 8° C., treating the purified supernatant containing Factor VIII with a solution containing ammonium sulfate, ammonium sulfate-glycine, sodium sulfate, sodium sulfate-sodium citrate, ammonium sulfate-sodium citrate, citrate-glycine at a concentration of 8 to 35% and a pH of 5.6 to 6.8 so as to precipitate a Factor VIII containing precipitate, dissolving the precipitated Factor VIII containing precipitate in a sodium chloride-sodium citrate buffer solution containing an antithrombin-heparinoid or antithrombin-III-heparinoid complex as well as albumin, ultrafiltering or dialyzing, lyophilizing and inactivating by heat treatment.

The invention will now be explained in more detail by the following examples.

EXAMPLE 1

From 16.5 l plasma, 150 g cryoprecipitate were recovered by deepfreezing and rethawing. The latter was dissolved in 900 ml trisodium citrate buffer containing 90 mg sulfated polysaccharide "SP 54" (Benechemie), 9 units of Atheplex as well as 27,000 units of aprotinin. The pH of the solution was adjusted to 6.25, the temperature was adjusted to 4° C., undesired proteins being precipitated and separated by centrifugation. The supernatant was slowly admixed with glycine and ammonium sulfate under stirring at a pH of 6.0 to 6.3 and at room temperature until a precipitation concentration of 120 g/l glycine and 85 g/l ammonium sulfate had been reached.

The precipitate formed was separated by centrifugation, dissolved in a sodium chloride-citrate buffer and dialyzed against the same buffer. The dialysate was admixed with glycine and albumin to a concentration of 10 mg/ml glycine and 2 mg/ml albumin and the solution was lyophilized. A portion of the powdery lyophilisate obtained was adjusted with steam to a moisture content of 8 w/w % and another portion was adjusted to a moisture content of 24 to 26 w/w %.

These moistened preparations were subjected to heat treatment at 60° or 70° C. for a period of 10 to 100 hours in closed containers under nitrogen atmosphere so as to inactivate possibly present viruses. Subsequently, the specific Factor VIII activity was determined. The results as compared to the non heat-inactivated lyophilisate produced according to Example 1 are to be taken from the following Table I.

TABLE I

|  | Example 1 according to invention |
|---|---|
| Factor VIII, lyophilisate, not heated | 54.7 U/ml 100% |
| specific activity | 4.31 U/mg |
| content of IgG per 1000 units Factor VIII | 1.8 mg |

TABLE I-continued

|  | Example 1 according to invention |
|---|---|
| Factor VIII, lyophilisate with moisture content 7.9% | |
| after 10 h heated at 60° C. | 53.6 U/ml 98% |
| after 70 h heated at 60° C. | 42.5 U/ml 78% |
| after 100 h heated at 60° C. | 40.0 U/ml 73% |
| after 10 h heated at 70° C. | 43.3 U/ml 79% |
| Factor VIII, lyophilisate with moisture content 25.2% after 10 h heated at 60° C. | 45.0 U/ml 82% |

EXAMPLE 2

In order to illustrate the superiority of the preparations produced according to the invention over known ones (e.g., known from U.S. Pat. No. 4,522,751) with regard to thermal stability, the first part of Example 1 was repeated; yet, instead of the precipitation with glycine and ammonium sulfate, 8% ethyl alcohol in the presence of 1.45 mol/l glycine was used at a pH of 6.0. The precipitate was separated, dissolved in a citrated NaCl-glycine-albumin buffer, lyophilized and the lyophilisate was readjusted to a moisture content of 8 w/w % and 24 to 26 w/w %, respectively, with steam and, as described in connection with Example 1, was heated under nitrogen atmosphere. The results are indicated in the following Table II, with the elevated IgG content (30 mg as compared to 1.8 mg) being significant on the one hand, and with the specific activities present after heat treatment, in particular after long-term heating, of the comparative prior art example being clearly lower, on the other hand.

TABLE II

|  | Comparative Example |
|---|---|
| Factor VIII, lyophilisate, not heated | 54.3 U/ml 100% |
| specific activity | 2.69 U/mg |
| content of IgG per 1000 units of Factor VIII | 30 mg |
| Factor VIII, lyophilisate with moisture content 7.9% | |
| after 10 h heated at 60° C. | 50.5 U/ml 93% |
| after 70 h heated at 60° C. | 24.4 U/ml 45% |
| after 100 h heated at 60° C. | 26.6 U/ml 49% |
| after 10 h heated at 70° C. | 29.3 U/ml 54% |
| Factor VIII, lyophilisate with moisture content 25.2% after 10 h heated at 60° C. | 24.4 U/ml 45% |

EXAMPLE 3

The first part of Example 1 was repeated; yet a salt combination of NaCl and ammonium sulfate in an aqueous solution was used to precipitate the Factor VIII concentrate until a precipitation concentration of 10% NaCl and 12% ammonium sulfate had been reached. Further processing, centrifugation, dissolution, dialyzation, lyophilization and moistening were effected as in Example 1. The results are indicated in Table III.

TABLE III

| Factor VIII, lyophilisate, not heated | 42.6 U/ml 100% |
|---|---|
| specific activity | 3.18 U/mg |
| content of IgG per 1000 units Factor VIII | 9 mg |
| Factor VIII, lyophilisate with moisture content 8% after 10 h heated at 70° C. | 30 U/ml 71% |

TABLE III-continued

| | | |
|---|---|---|
| Factor VIII, lyophilisate with moisture content 24.6% | 32 U/ml | 75% |

EXAMPLE 4

The first part of Example 1 was repeated; yet, a salt combination of sodium citrate and ammonium sulfate in an aqueous solution was used to precipitate the Factor VIII concentrate until a precipitation concentration of 5% sodium citrate and 12.5% ammonium sulfate had been reached. Further processing, centrifugation, dissolution, dialyzation, lyophilization and moistening were effected as described in Example 1. The results are indicated in Table IV.

TABLE IV

| | | |
|---|---|---|
| Factor VIII, lyophilisate, not heated | 42.2 U/ml | 100% |
| specific activity | 3.49 U/mg | |
| content of IgG per 1000 units Factor VIII | 2.6 mg | |
| Factor VIII, lyophilisate with moisture content 8.3% after 10 h heated at 70° C. | 32.8 U/ml | 78% |
| Factor VIII, lyophilisate with moisture content 27.1% after 10 h heated at 60° C. | 34.5 U/ml | 82% |

EXAMPLE 5

The first part of Example 1 was repeated; yet, a salt solution of ammonium sulfate was used to precipitate the Factor VIII concentrate until a precipitation concentration of 13.2% ammonium sulfate had been reached. Further processing, centrifugation, dissolution, dialyzation, lyophilization and moistening were effected as described in Example 1. The results are indicated in Table V.

TABLE V

| | | |
|---|---|---|
| Factor VIII, lyophilisate, not heated | 48.6 U/ml | 100% |
| specific activity | 5.70 U/mg | |
| content of IgG per 1000 Factor VIII | 0.6 mg | |
| Factor VIII, lyophilisate with moisture content 7.7% after 10 h heated at 70° C. | 28.9 U/ml | 59% |
| Factor VIII, lyophilisate with moisture content 23.7% after 10 h heated 60° C. | 39.2 U/ml | 81% |

In all cases, the IgG content of the Factor VIII concentrate obtained is far below 10 mg and the residual activities still present upon heat treatment are more than 70%.

What we claim is:

1. A method of producing a Factor VIII (AHF) containing fraction having a specific activity of at least 2.5 units of Factor VIII/mg protein as well as a portion of immunoglobulin G (IgG) of 10 mg/1000 units of Factor VIII at the most, with the risk of transmission of viral or bacterial infections being avoided or largely reduced when applied therapeutically or prophylactically, which method comprises in combination:
   preparing a first solution of a Factor VIII containing plasma fraction including at least one of the group consisting of heparinoid and a complex compound of heparin and antithrombin III (Atheplex),
   precipitating and separating undesired proteins from said first solution in the presence of sulfated polysaccharides at a pH of 6.0 to 6.4 and at a temperature of 0° to 25° C. so as to obtain a purified Factor VIII containing supernatant,
   treating said purified Factor VIII containing supernatant with a protein precipitating agent selected from the group consisting of ammonium sulfate, ammonium sulfate-glycine, sodium chloride-glycine, sodium sulfate, sodium sulfate-sodium citrate, ammonium sulfate-sodium citrate, sodium chloride-ammonium sulfate at a concentration of 8 to 35% and a pH of 5.6 to 6.8 so as to precipitate a Factor VIII containing precipitate,
   dissolving said Factor VIII containing precipitate in a buffer solution so as to obtain a second solution,
   one of ultrafiltering and dialyzing said second solution, and lyophilizing so as to obtain a lyophilisate, and
   heat-treating said lyophilisate at a temperature and for a period of time sufficient to inactivate possibly present viruses.

2. A method as set forth in claim 1, wherein said lyophilisate is adjusted to a water content of more than 0.05 (5% by weight) and less than 0.70 (70% by weight) and is treated in a closed container at a temperature ranging from 50° to 121° C. under steam partial-pressure elevation.

3. A method as set forth in claim 2, wherein said water content is adjusted to less than 0.40 (40% by weight).

4. A method as set forth in claim 1, wherein said lyophilisate is treated with steam at a pressure of 0.01 to 2 bar for a period of time up to 100 hours.

5. A method as set forth in claim 1, wherein said viruses are reproductive filterable pathogens selected from the group consisting of hepatitis viruses and HIV (human immune deficiency viruses).

6. A method as set forth in claim 1, wherein precipitating of said Factor VIII containing solution with said protein precipitating agent is carried out at a pH of 5.6 to 6.8 and at a temperature of 1° to 40° C.

* * * * *